United States Patent [19]

Takagi et al.

[11] Patent Number: 4,857,460

[45] Date of Patent: Aug. 15, 1989

[54] CYCLOHEXIMIDE RESISTANT GENE

[75] Inventors: Masamichi Takagi, Fuchu; Keiji Yano, Tokyo; Ichiro Shibuya; Minoru Morikawa, both of Kashiwa, all of Japan

[73] Assignee: Nikka Whisky Distilling Co., Ltd., Tokyo, Japan

[21] Appl. No.: 808,121

[22] Filed: Dec. 12, 1985

[30] Foreign Application Priority Data

Aug. 27, 1985 [JP] Japan ................................ 60-188291

[51] Int. Cl.$^4$ .................... C12N 5/00; C12N 15/00; C12P 19/34
[52] U.S. Cl. .................... 435/91; 435/172.1; 435/172.3; 435/320; 435/255; 536/27
[58] Field of Search .................. 536/27; 435/68, 70, 435/172.1, 172.3, 255, 256, 320, 921; 935/28, 10, 14, 37, 56, 69

[56] References Cited

PUBLICATIONS

Takagi et al., Jun. 1985, *J. Gen. Appl. Micro.*, vol. 31 (3), pp. 267–276, "Induction of cycloheximide resistive on *Candida maltosa* by modifying the ribosomes".
Kaufer et al., *Nucl. Acids Res.*, vol. 10 (10), 1983, pp. 3123–3135, "Cycloheximide resistance in yeast: the gene and its protein".
Fried et al., *Nucl. Acids Res.*, vol. 10 (10), 1982, pp. 3133–3148, "Molecular cloning and analysis of yeast gene for cycloheximide resistance and ribosomal protein L29".
Gillum et al., *Mol Gen. Genet.*, vol. 198, pp. 179–182, 1984, "Isolation of the *Candida albicans* gene for orotidine–5–phosphate decarboxylase by complementation".
Brown et al., *Methods Enzymol*, vol. 101, pp. 278–290, 1983, "Yeast vectors with negative selection".
Takagi et al., *J. Bact.*, Oct. 1986, pp. 417–419, vol. 168 (1), "Cloning in *Saccharomyces cereviviace* of a cycloheximide resistance gene from the *Candida maltosa* gene which modifies ribosomal".

*Primary Examiner*—Robin Teskin
*Attorney, Agent, or Firm*—Armstrong, Nikaido, Marmelstein, Kubovcik & Murray

[57] ABSTRACT

A cycloheximide resistant gene of the present invention can be produced by cultivating yeast belonging to Candida genus and by cleaving a cycloheximide resistant gene from the yeast using restriction enzymes XbaI and Sau3AI.

By incorporating the cycloheximide resistant gene together with the gene for useful substance into a plasmid, the transformant producing useful substance can be readily detected.

6 Claims, 5 Drawing Sheets

CYCLOHEXIMIDE RESISTANT GENE

BACKGROUND OF THE INVENTION

This invention concerns a cycloheximide resistant gene, a process for producing the same, a recombinant DNA vector containing the resistant gene and a transformant containing the resistant gene.

It has been known that cycloheximide is an antibiotic which inhibits the protein synthesis of various eukaryotes by binding to the subunit proteins of 60S (precipitation constant) ribosome.

On the other hand, mutation changing the cycloheximide sensitivity of ribosome has been reported in several eukaryotes up to now.

Although wild-type *Saccharomyces cerevisiae* is sensitive to cycloheximide, several cycloheximide resistant variants have been isolated. For example, it has been shown that a change in the structural gene coding the ribosome protein causes the cycloheximide resistance and cyh2 variant (Walter Stöckleim and Wolfgang Piepersberg, Current Genetics, 1, 177–180 (1980)).

Further, wild-type *Kluyveromyces fragilis* itself, a yeast, is cycloheximide resistant. In this case, it has also been demonstrated that the ribosome protein is not sensitive to cycloheximide.

These data suggest that the cycloheximide resistance is determined by the structure of several genes coding for the ribosome protein, in addition to the resistance acquired due to the change in the membrane permeability of chemicals as discussed by Adoutte-Panvier and Davies, *Mol. Gen. Genet.* 194, 310 (1984).

In view of the above, there has been a demand for the gene rendering the ribosome protein resistant to cycloheximide and providing for the protein synthesis free from cycloheximide inhibition for the protein synthesis.

SUMMARY OF THE INVENTION

This invention provides a cycloheximide resistant gene represented by the following base sequence:

| | |
|---|---|
| CTAGAGCACA | ATTATTATTC |
| AACGTTATTA | CAAACAAGCA |
| TATTGAATTG | GAATATTTTT |
| GGTTGGTTTA | AAAAAAAAAT |
| CCAAAACATA | AAAAAAATAA |
| ATTGTGTGAC | AAAAAAATGT |
| ACGTTTATCT | ACAGAATAAG |
| GAAGTTGTAA | AGAAAACCCA |
| TACACACACA | CACCCCCGCT |
| AAAATATTAT | ATAAATAAAC |
| CATGAGTTTT | CCAAATTTTT |
| CAAAAAAAA | ATTCCCCCTT |
| TTTCTTTTAG | AAAAGATTCC |
| TTAATTTGTG | CATTACTTTC |
| TGATTTTGCT | AGACTGATAC |
| TATGGGTACG | TAATTGAATC |
| AATTGTTATC | TGACGTTCTC |
| AAAATATGCT | AACCAAAAAC |
| TAGTTAATAT | TCCAAAAACA |
| AGAAATACTT | ATTGTAAAGG |
| AAAGGGTGT | CGTAAACATA |
| CGATTCACAA | GGTGACTCAA |
| TACAAATCAG | GTAGAGCTTC |
| CTTATTTGCT | CAAGGTAAAA |
| GAAGATACGA | TAGGAAACAA |
| TCTGGGTATG | GTGGTCAAAC |
| AAAGCAAGTT | TTCCATAAGA |
| AGGCTAAAAC | GACTAAGAAG |
| ATTGTGTTGA | AGTTGGAATG |
| TACTGTTTGT | AAAACCAAGA |
| AACAATTGCC | ATTGAAAAGA |
| TGTAAACATA | TTGAATTGGG |

| -continued | |
|---|---|
| TGGTGAAAAA | AAACAAAAAG |
| GTCAAGCATT | ACAGTTCTAG |
| GTACATGTTG | TATATATTTT |
| GCATTATCCC | CAATAATACA |
| AGAAAGAAGA | CAAAACTAGT |
| TTTGTAGATT | GTAATAGTAA |
| TTTCTGTATG | TGTGTGTTTT |
| TCTTTTTTTT | GCAGATTACA |
| CACGTCAAAA | AAATGATTAA |
| ACACACACGC | AACACTTTTT |
| TTTCTTTCCT | TTGAACAAGA |
| AATCAACAAC | AAACACCTTA |
| AAAGGAGGAA | AAAAAAAATT |
| CGCTTATTTC | CTTTCACTCT |
| CTATTACATA | TCACCACTAA |
| TATTTAACAT | TTCAATCACC |
| ATCCCAACTA | ACATTCATTT |
| CCTTATATAC | ACCTTTTCTT |
| TATCTTTATT | CTAGCATCTA |
| CACCCATAAA | TAACTGACTT |
| CATTCACTAC | AACCATTCCT |
| CATATCATTT | CATTTCTTTT |
| TCAACAACTT | TTTTTTTTTC |
| AAATCAAAGT | TTTACTGTCC |
| ATAGATAATG | AACTTTGATC |

This invention further provides a process for producing a cycloheximide resistant gene represented by the above-mentioned base sequence, a recombinant DNA vector containing the above-mentioned gene, a transformant and *Candida maltosa* containing the above-mentioned gene.

Since this invention provides a gene for giving resistance to cycloheximide which is an antibiotic substance inhibiting the protein synthesis, a process for producing the gene and the like, a transformant producing useful substance can be detected easily by incorporating the resistant gene together with the gene for useful substance into the plasmid.

Further, presence of the vector containing the resistant gene in the cells can easily be detected as the expression of the resistance by the addition of the cycloheximide into media, and it can also be used as a vector marker.

DETAILED DESCRIPTION OF THE INVENTION

Figure 1:
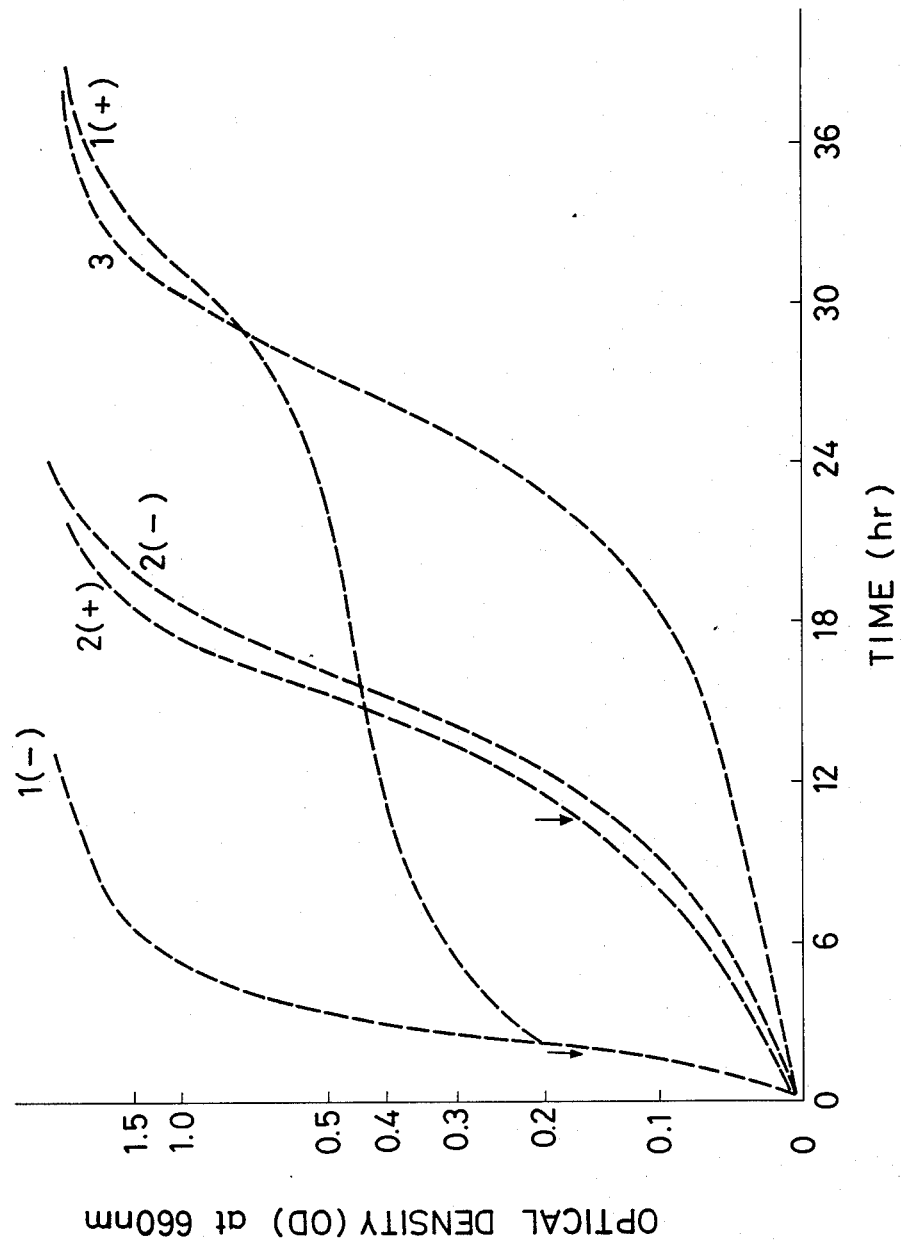
FIG. 1 is a graph showing the effect of cycloheximide (CYH) on the multiplication of *Candida maltosa;*

The cycloheximide resistant gene, the recombinant DNA vector incorporating the same and the transformant containing the resistant gene can be produced, for example, as described below.

Yeast belonging to Candida genus is cultivated on MY medium. (Difco).

After the elapse of a predetermined of time, a cycloheximide resistant gene is cleaved from the yeast by using restriction enzymes XbaI and Sau3AI.

The gene segments are inserted into plasmid YEp13 by using T4-DNA ligase to prepare a new recombinant vector. The new recombinant vector is inserted into the cell sensitive to cycloheximide by the known method such as a protoplast transforming method of Hinnen et al. (Hinnen, A. Hicks, J. B., Fink, G. R., Proc. Natl. Acad. Sci. USA 75, 1929 (1978)) or a lithium metal transforming method of Ito et al. (Ito, H., Fukada, Y., Murata, A., J. Bacteriol. 153, 165 (1983)) and the like.

Any of yeasts belonging to the Candida genus can be used herein, for example *Candida maltosa* IAM12247, IAM12248, etc., and *Candida gillermondii*, IFO0566, etc.

The cycloheximide resistant gene is taken out from the yeast by the method as described below.

After extracting whole DNA from the cultivated cells and purifying it, it is cleaved into smaller segments, for example, by using a restriction enzyme such as SAu-3AI and, thereafter, linked to vector plasmid YIp13 to prepare a gene library.

Then, the *Saccharomyces cerevisiae* yeast is transformed with the gene library, cultivated on a medium containing cycloheximide at 30° C. and, after several days, colonies formed are separated. They are again cultivated in a medium containing cycloheximide and the plasmid is extracted from the cells.

Then, the plasmid thus obtained is cleaved by using an appropriate restriction enzyme, for example, Sau3AI and XbaI, to separate the cycloheximide resistant gene derived from the Candida yeast.

Then, the cycloheximide resistant gene is inserted into the plasmid to prepare a recombinant DNA vector, by cutting the vector using a restriction enzyme and connecting the cycloheximide resistant gene by the use of T4-DNA ligase.

The base sequence of the new cycloheximide resistant gene according to this invention is determined by the known dideoxy process of Sanger et al., using M13 phage (Sanger, F., Nicklen, S. and Coulson, A. R. Proc. Natl. Acad. Sci. USA, 74, 5463–5467 (1977)) (Messing, J., Methods in Enzymology-recombinant DNA, Part C, 101, 20–78 (1983)).

As the use or application examples of the cycloheximide resistant gene, the following can be considered.

The cycloheximide resistant gene is incorporated into a plasmid vector used in the yeast. The vector is transferred into the CYH-sensitive bacteria (for example, *Saccharomyces cerevisiae*) and the CYH-resistant transformants can be isolated because they are able to grow on a medium containing cycloheximide.

Now, a gene of other useful substance is incorporated into the vector with the cycloheximide resistant gene. Then, when the cycloheximide resistant transformant is separated in the same manner as described above, it has a capability of producing the useful substance.

EXAMPLE

This invention will now be described more specifically referring to various examples.

EXAMPLE 1

FIG. 1 shows that the multiplication of *Candida maltosa* IAM12247 is inhibited by addition of cycloheximide (CYH) and then recovered therefrom after a certain period of time.

*Candida Maltosa* IAM12247 was grown with shaking in an L-shaped tube at 30° C. on a synthetic medium as shown below.

Synthetic medium composition (per one liter)

| | |
|---|---|
| NH$_4$Cl | 2.5 g |
| KH$_2$PO$_4$ | 21.0 g |
| Na$_2$HPO$_4$.12H$_2$O | 6.0 g |
| MgSO$_4$.7H$_2$O | 0.2 g |
| NaCl | 0.1 g |
| yeast extract | 0.1 g |
| FeSO$_4$ | 5.0 mg |
| ZnCl$_2$ | 0.5 g |
| CoCl$_2$ | 1.0 mg |
| CaCl$_2$ | 0.5 mg |
| Na$_2$MoO$_4$ | 0.5 mg |
| CuSO$_4$ | 1.0 mg |
| glucose | 10.0 g |
| pH 5.9 | |

The growth curves were automatically recorded by the variation in the light absorption at the wavelength of 660 nm. Each of the curves represents as below:

Curve
1 (−): no cycloheximide was added
1 (+): cycloheximide was added by 700 μg/ml at the time shown by the arrow
2 (−): cycloheximide was added by 25 μg/ml
2 (+): cycloheximide was added by 25 μg/ml. After multiplication, cycloheximide was further added by 700 μg/ml at the time shown by the arrow
3: cycloheximide was added by 700 μg/ml

EXAMPLE 2

The capability of cycloheximide-treated and non-treated cells of *Candida maltosa* IAM12247 of poly U-directed protein synthesis was examined in the presence of cycloheximide.

The cycloheximide-treated cells were obtained by growing the cells on MY medium (containing 3 g of yeast extract, 3 g of malt extract and 5 g of bactopepton per one liter) in the presence of 50 μg/ml of cycloheximide. The non-treated cells were grown only on MY medium.

Both of the yeast cells were suspended in the homogenizing buffer (containing 8.5% mannitol, 2 mM Mg-acetate, 30 mM Hepes/KOH, pH 7.4, 2 mM dithiothreitol and 100 mM K-acetate) so as to provide 1 g wet cell weight/1.25 ml of the medium and the cells were disrupted by vigorously shaking by hands with 3–4 g of glass beads (from 0.45 to 0.5 mm in diameter) for one minute, three times.

The crude yeast cell extract was centrifugated at 1000 rpm for 2 minutes, and the supernatant was further centrifugated at 30,000×g for 20 minutes to obtain a clear supernatant. The thus obtained clear supernatant was kept at 20° C. for 10 minutes in the presence of 0.5 mM ATP to decompose the endogenous mRNA. Thereafter, the ribosome fraction was passed through a column of Sephadex G-25 (manufactured by Pharmacia Co., Sweden) (equilibrated with the buffer containing 2 mM Mg-acetate, 30 mM Hepes/KOH, pH 7.4, 2 mM dithiothreitol and 100 mM of K-acetate).

Figure 2:
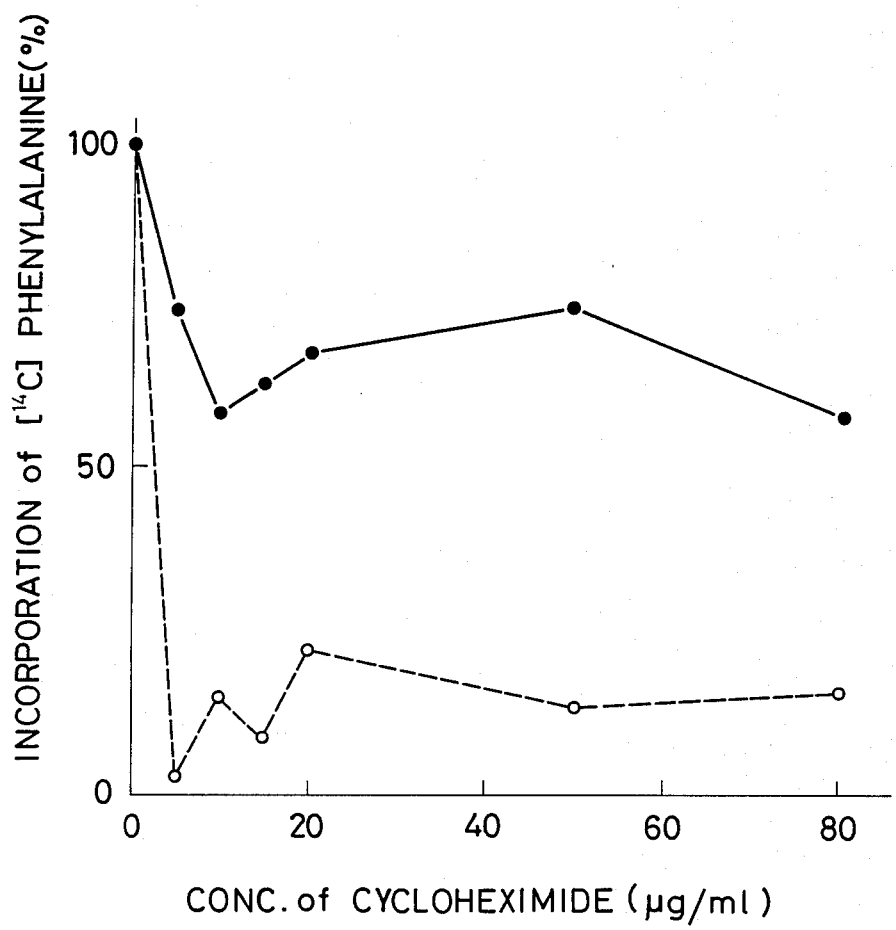
FIG. 2 is a graph showing the capability of polyU protein synthesis of cycloheximide resistant and sensitive strains of *Candida maltosa* in the presence of CYH.

By using the ribosome fraction prepared as above, inhibition of the capability of poly U-directed polypeptide synthesis (polyphenylalanine) by cycloheximide was measured in the reaction solution and at the reaction temperature as described below. The results are shown in FIG. 2.

REACTION SOLUTION (100 μL)

30.8 mM, Hepes/KOH buffer solution, pH 7.4
2.5 mM, Mg-acetate
220.0 mM, K-acetate
2.7 mM, dithiothreitol
0.5 mM, ATP
0.1 mM, GTP
20.0 mM, creatine phosphate
20.0 μg, creatine kinase
2.0 mM glucose-6-phosphate
125.0 μg, poly U
2 unit, ($OD_{260}$) ribosome fraction
1 μCi
   ($^{14}C$) phenylalanine
   (504 mCi/mmol)

REACTION TEMPERATURE: 20° C.

An aliquote of 10 μl was removed at various times during the reaction to determine the radioactivity in the hot-acid insoluble fraction.

In the figure, (●—●) shows the protein synthesis capability of the cycloheximide resistant cells and (○—○) shows the protein synthesis capability of the cycloheximide sensitive cells.

EXAMPLE 3

This experiment shows the resistance acquired due to the modification of the ribosome in the cycloheximide resistant *Candida maltosa* IAM12247.

After crude ribosome fraction obtained by using Sephadex G-25 (refer to Example 2) was treated with 0.8% Triton X-100 and 0.75M KCl, the treated fraction was centrifugated at 20,000 rpm for 20 minutes. The supernatant was further centrifugated at 30,000 rpm for 4.5 hours and the precipitated fractions (ribosome) was used for this experiment.

The soluble fraction (other than ribosome) required for the protein synthesis was prepared by the following method. That is, after addition of 7.5 g of ammonium sulfate to 150 ml of crude yeast extract, the resultant suspension stood overnight and it was centrifugated at 13,000 rpm for 30 minutes. The precipitates were recovered, dissolved in a buffer solution (10 mM Tris-HCl at pH 7.6, 10 mM $MgCl_2$, 10 mM 2-mercaptoethanol, 10% (v/v) glycerol) and then dialyzed against the same buffer solution.

Figure 3:
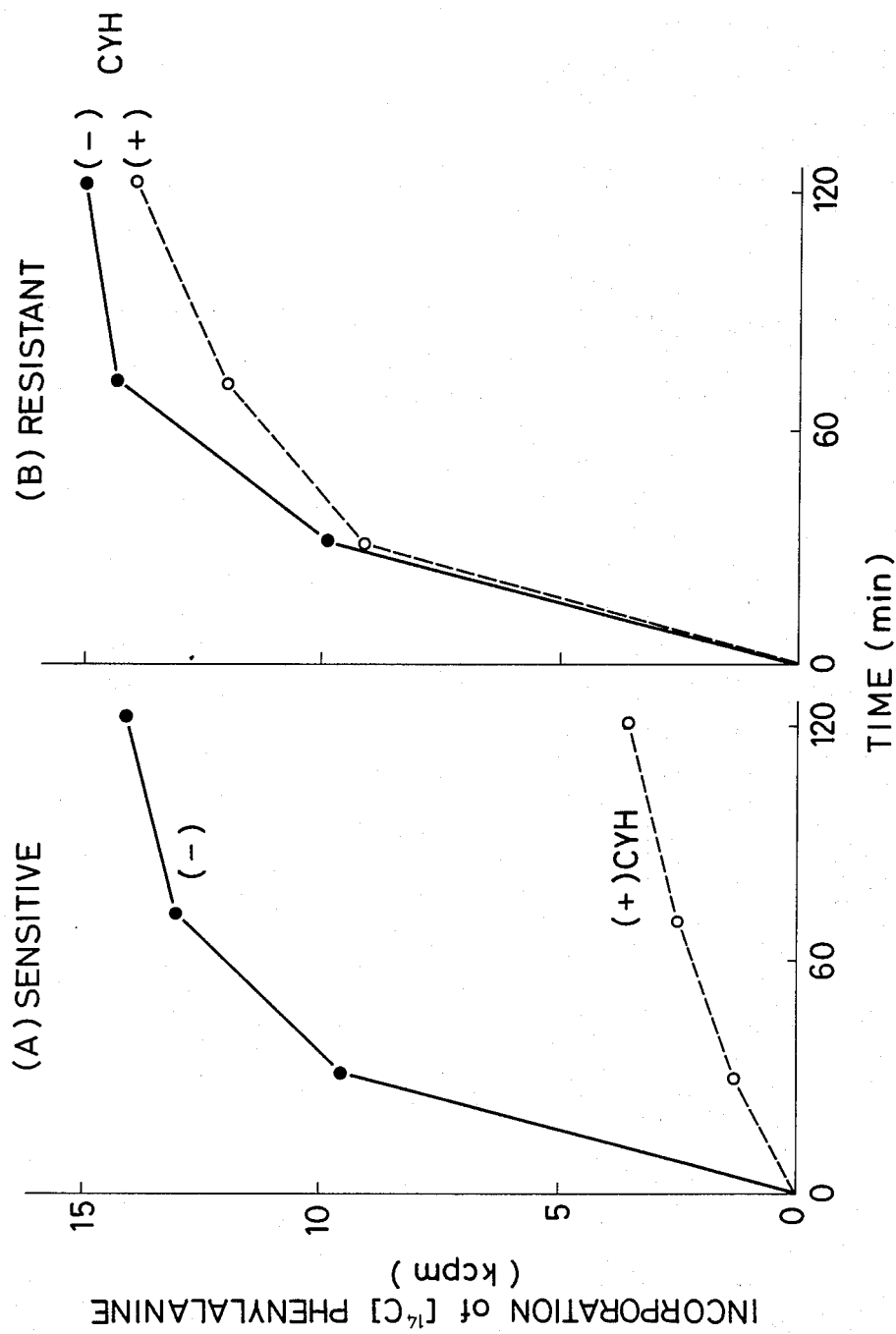
FIG. 3 is a graph showing the capability of protein synthesis of the CYH resistant and sensitive strains of *Candida maltosa;*

Glycerol was added to the sample solution (S-100 fraction) to make up to the concentration of 25% for storage at −80° C. The protein synthesis capability was measured using the ribosome and the S-100 fraction thus prepared by the following methods. The results are shown in FIG. 3 and Table-1.

REACTION SOLUTION (100 μL)

50.0 mM, Tris-HCl, pH 7.6
40.0 mM, KCl
8.0 mM, Mg-acetate
5.0 mM, phosphoenol pyruvate
1.4 mM, ATP
0.17 mM, GTP 5.0 mM, 2-mercaptoethanol
1.0 mM, spermidine
0.5 mM, dithiothreitol
2.5%, (v/v) glycerol
100–125 μg, poly U
1 unit, ($OD_{260}$) yeast tRNA
1 unit, ($OD_{260}$) ribosome
0.1 unit, ($OD_{260}$) S-100 fraction
1 μCi, ($^{14}C$) phenylalanine

REACTION TEMPERATURE: 30° C.

After the reaction of 20 l of the solution was removed to measure the radioactivity in the hot acid insoluble fraction.

(I) FIG. 3 shows the effect of poly U-directed translation of CYH-sensitive and resistant ribosomes from *Candida maltosa* using the S-100 fraction prepared from CYH-sensitive *Saccharomyces cerevisiae* AH22 strain, and (II) Table-1 shows the effect of poly U-directed translation consisting of ribosomes and the S-100 fraction prepared from both of CYH-sensitive and resistant *Candida maltosa* IAM12247.

TABLE 1

Effect of CYH on the poly U-directed translation system consisting of ribosomes and S-100 fraction prepared from *Candida maltosa* IAM12247

| Fraction | S-100 fraction prepared from resistant *Candida maltosa* | S-100 fraction prepared from sensitive *Candida maltosa* |
|---|---|---|
| Ribosome prepared from resistant *Candida maltosa* | 105%* | 89% |
| Ribosome prepared from sensitive *Candida maltosa* | 21% | 31% |

*$\frac{\text{synthesis in the presence of CYH (50 μg/ml)}}{\text{synthesis in the absence of CYH}} \times 100$ where CYH represents cycloheximide.

EXAMPLE 4

This example shows the result of the experiment for transforming *Saccharomyces cerevisiae* using a plasmid containing a cycloheximide resistant gene.

In this experiment, two kinds of plasmids YEp13 and YRp7 were used.

Firstly, the plasmid vector YEp13 was cleaved by a restriction enzyme BamHI and the cyclohexmide resistant gene was linked by using a T4-DNA ligase to prepare plasmid YEp-CYH.

The plasmid was transformed into yeast of *Saccharomyces cerevisiae* AH22 strain (leu−) by using the method of Hinnen et al. and the cells were embedded into 10 ml of a nutrient agar medium containing 1.2M sorbitol (YPD medium: 1% yeast extract, 2% polypepton, 2% glucose, 3% agar). After cultivating at 30° C. for 18 hours, they were overlaid with 10 ml of a nutrient agar medium containing 10 μg/ml of cycloheximide and then cultivated at 30° C. for 4–5 days.

As the result of the cultivation, several colonies were formed. YEp-CYH was recovered from these colonies as plasmids. These results showed that it could be confirmed that this cycloheximide resistant gene can be used as the marker upon transformation using the YEp type vector of the yeast.

Secondary, the vector YRp7 was cleaved in the same manner as above by using a restriction enzyme BamHI and the cycloheximide resistant gene was linked to the YRp7 cleaved site by using a T4-DNA ligase to prepare plasmid YRp-CYH. This plasmid was transformed into the yeast of *Saccharomyces cerevisiae* D13-1A strain (trp−) by the lithium metal transforming method of Ito et al. Then, after cultivating by the over-lay method containing cycloheximide in the same manner as described above, colonies were formed. Plasmid was extracted from the colonies and YRp-CYH could be recovered.

From the above experiment, it could be confirmed that this cycloheximide resistant gene can be useful as a marker upon transformation using the YRp type vector.

EXAMPLE 5

Figure 4:
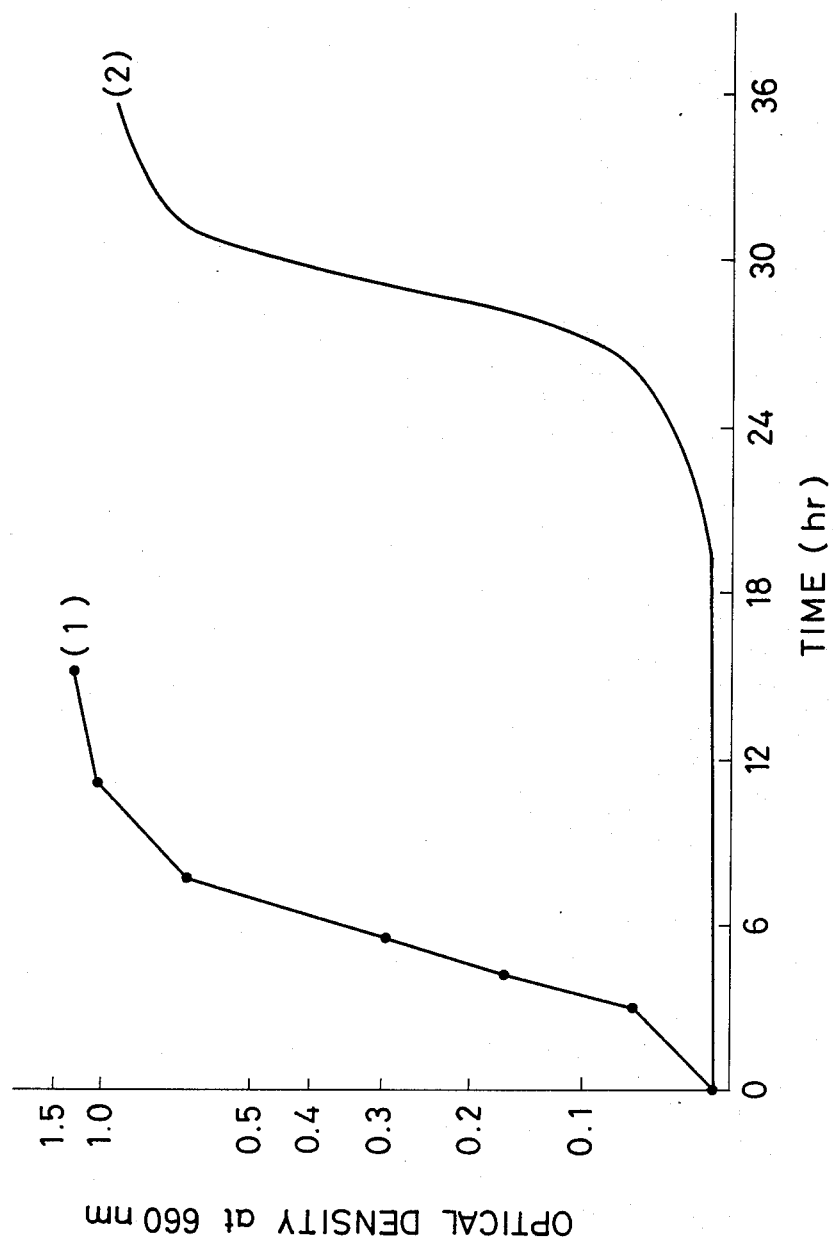
FIG. 4 is a graph showing induction of the CYH resistance of *Candida gillermondii.

This experiment shows the induction of the cycloheximide resistance of *Candida gillermondii*-IFO0566. After 10 ml of MY culture was incubated with shaking in an L-shaped tube overnight for sufficient multiplication, a portion of culture was transferred to 10 ml of new MY culture to make up to 1% in volume and then subjected to shaking cultivation under the following conditions. The growth curves were recorded by the change in the light absorption at 660 nm wavelength. The results are shown in FIG. 4.

The curves represent:
(1): with no addition
(2): cycloheximide added by 25 μg/ml

EXAMPLE 6

After partially decomposing the whole DNA of *Candida maltosa* IAM 12247 by using a restriction enzyme Sau3AI, DNA fragments were linked to the vector YEp13 having been cleaved by a restriction enzyme BamHI by using T4-DNA ligase.

The product was transferred into the yeast of Saccharomyces cerevisiae AH22 strain by using lithium metal transforming method of Ito et al.

After transplanting the transformant to a culture containing cycloheximide, it was cultivated at 30° C. and, after several days colonies of transformants were separated. Then, the plasmid DNA was extracted from the strain acquiring the cycloheximide resistance and referred to as pCYH.

Further, the transformant was referred to AH22 (pRIM-C).

*Saccharomyces cerevisiae* AH22 (pRIM-C) was subjected to shaking cultivation in a synthetic culture containing leucine by using an L-shaped tube for two days and grown sufficiently.

Figure 5:
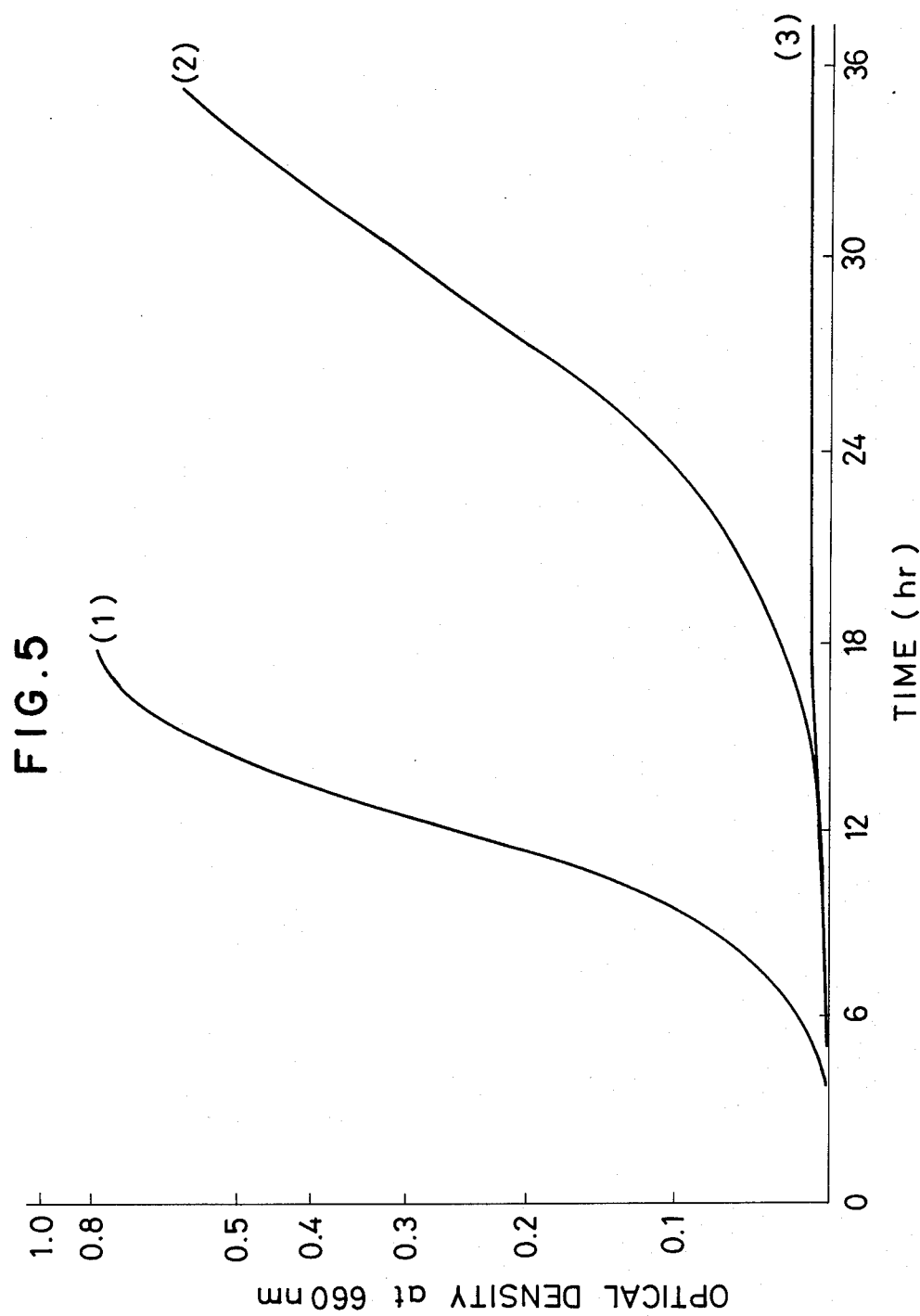
* and FIG. 5 is a graph showing growth curve of the transformant described in this invention and non-transformant in the presence of CYH.

Then, the cell suspension was transplanted by 1% to a new YPD medium and cultivated under the following conditions. The growth was traced due to the change in the light absorption at the wavelength of 660 nm. The results are shown in FIG. 5.

The curves represent:
(1): with no addition of cycloheximide
(2): cycloheximide added by 5 μg/ml
(3): not-transformant was grown in the presence of cycloheximide.

When 700 μg/ml of cycloheximide was added at the light absorption (OD$_{660}$)=0.3 under the condition (2), growth was not substantially inhibited but kept continued.

What is claimed is:

1. An isolated cycloheximide resistant gene, comprising a base sequence of

| | |
|---|---|
| CTAGAGCACA | ATTATTATTC |
| AACGTTATTA | CAAACAAGCA |
| TATTGAATTG | GAATATTTTT |
| GGTTGGTTTA | AAAAAAAAAT |
| CCAAAACATA | AAAAAAATAA |
| ATTGTGTGAC | AAAAAAATGT |
| ACGTTTATCT | ACAGAATAAG |
| GAAGTTGTAA | AGAAAACCCA |
| TACACACACA | CACCCCCGCT |
| AAAATATTAT | ATAAATAAAC |

-continued

| | |
|---|---|
| CATGAGTTTT | CCAAATTTTT |
| CAAAAAAAAA | ATTCCCCCTT |
| TTTCTTTTAG | AAAAGATTCC |
| TTAATTTGTG | CATTACTTTC |
| TGATTTTGCT | AGACTGATAC |
| TATGGGTACG | TAATTGAATC |
| AATTGTTATC | TGACGTTCTC |
| AAAATATGCT | AACCAAAAAC |
| TAGTTAATAT | TCCAAAAACA |
| AGAAATACTT | ATTGTAAAGG |
| AAAAGGGTGT | CGTAAACATA |
| CGATTCACAA | GGTGACTCAA |
| TACAAATCAG | GTAGAGCTTC |
| CTTATTTGCT | CAAGGTAAAA |
| GAAGATACGA | TAGGAAACAA |
| TCTGGGTATG | GTGGTCAAAC |
| AAAGCAAGTT | TTCCATAAGA |
| AGGCTAAAAC | GACTAAGAAG |
| ATTGTGTTGA | AGTTGGAATG |
| TACTGTTTGT | AAAACCAAGA |
| AACAATTGCC | ATTGAAAAGA |
| TGTAAACATA | TTGAATTGGG |
| TGGTGAAAAA | AAACAAAAAG |
| GTCAAGCATT | ACAGTTCTAG |
| GTACATGTTG | TATATATTTT |
| GCATTATCCC | CAATAATACA |
| AGAAAGAAGA | CAAAACTAGT |
| TTTGTAGATT | GTAATAGTAA |
| TTTCTGTATG | TGTGTGTTTT |
| TCTTTTTTTT | GCAGATTACA |
| CACGTCAAAA | AAATGATTAA |
| ACACACACGC | AACACTTTTT |
| TTTCTTTCCT | TTGAACAAGA |
| AATCAACAAC | AAACACCTTA |
| AAAGGAGGAA | AAAAAAAATT |
| CGCTTATTTC | CTTTCACTCT |
| CTATTACATA | TCACCACTAA |
| TATTTAACAT | TTCAATCACC |
| ATCCCAACTA | ACATTCATTT |
| CCTTATATAC | ACCTTTTCTT |
| TATCTTTATT | CTAGCATCTA |
| CACCCATAAA | TAACTGACTT |
| CATTCACTAC | AACCATTCCT |
| CATATCATTT | CATTTCTTTT |
| TCAACAACTT | TTTTTTTTC |
| AAATCAAAGT | TTTACTGTCC |
| ATAGATAATG | AACTTTGATC |

2. A recombinant DNA vector including a cycloheximide resistant gene of claim 1.

3. A transformant, comprising a cycloheximide sensitive yeast *Saccharomyces cerevisiae* into which a recombinant vector including a cycloheximide resistant gene of claim 1 is transferred.

4. *Candida maltosa* including a cycloheximide resistant gene of claim 1.

5. A process for producing a cycloheximide resistant gene according to claim 1, comprising:
(a) cultivating a yeast selected from the group consisting of *Candida maltosa* IAM 11247, IAM 12248 and *Candida gillermondii* IFO 0566 in a medium containing cycloheximide for a time period sufficient to induce resistance to cycloheximide;
(b) extracting the DNA from the yeast cells;
(c) digesting the extracted DNA with XbaI and Sau-3AI;
(d) preparing a gene library by annealing said digest into a cloning vector;
(e) transforming a cycloheximide sensitive yeast cell line with said gene library;
(f) culturing said transformed yeast cells in a medium containing cycloheximide; and
(g) isolating said cycloheximide resistant gene from the surviving colonies.

6. A process according to claim 5, wherein the cycloheximide resistant gene is obtained by restriction using the enzymes Sau3AI and XbaI.

* * * * *